United States Patent

Dill

(10) Patent No.: US 10,292,387 B1
(45) Date of Patent: May 21, 2019

(54) TICK REMOVAL OINTMENT

(71) Applicant: James Dill, Haverhill, MA (US)

(72) Inventor: James Dill, Haverhill, MA (US)

( * ) Notice: Subject to any disclaimer, the term of this patent is extended or adjusted under 35 U.S.C. 154(b) by 0 days.

(21) Appl. No.: 15/339,030

(22) Filed: Oct. 31, 2016

(51) Int. Cl.
*A01N 37/00* (2006.01)
*A01N 37/10* (2006.01)
*A01N 61/00* (2006.01)

(52) U.S. Cl.
CPC ............. *A01N 37/10* (2013.01); *A01N 61/00* (2013.01)

(58) Field of Classification Search
CPC ................................ A01N 37/10; A01N 61/00
USPC .......................................................... 514/537
See application file for complete search history.

(56) References Cited

U.S. PATENT DOCUMENTS

| | | | |
|---|---|---|---|
| 5,317,041 A | 5/1994 | Chapman et al. | |
| 5,414,014 A * | 5/1995 | Schneider | A61K 31/245 514/12.5 |
| D404,307 S | 1/1999 | Mohary et al. | |
| 6,696,078 B1 | 2/2004 | Masters | |
| 6,808,717 B1 | 10/2004 | Bale | |
| 8,323,672 B2 | 12/2012 | Schaffner et al. | |
| 2004/0223946 A1 | 11/2004 | Kidd, Jr. et al. | |

FOREIGN PATENT DOCUMENTS

EP 2772253 A1 * 9/2014 ........... A61C 19/063

* cited by examiner

*Primary Examiner* — Craig D Ricci
*Assistant Examiner* — Janet L. Coppins

(57) ABSTRACT

A tick removal ointment which is a topical composition having 25% benzocaine incorporated in white petroleum jelly. The amount of benzocaine in the tick removal ointment is efficacious for numbing the tick and hence causes the tick to release or self-extricate from the host mammal, optimally prior to the transmission of disease organisms from the tick to the host mammal. Upon the self-extrication of the tick from the host mammal, the white petroleum jelly is efficacious for killing the tick. Application of the present tick removal ointment eliminates the need to make direct contact with the tick to remove the tick and further eliminates the task of observing the mammal for a ii period of time because the composition is devised to first release the tick from the host mammal and then to kill the tick once the tick is released from the host mammal.

1 Claim, 1 Drawing Sheet

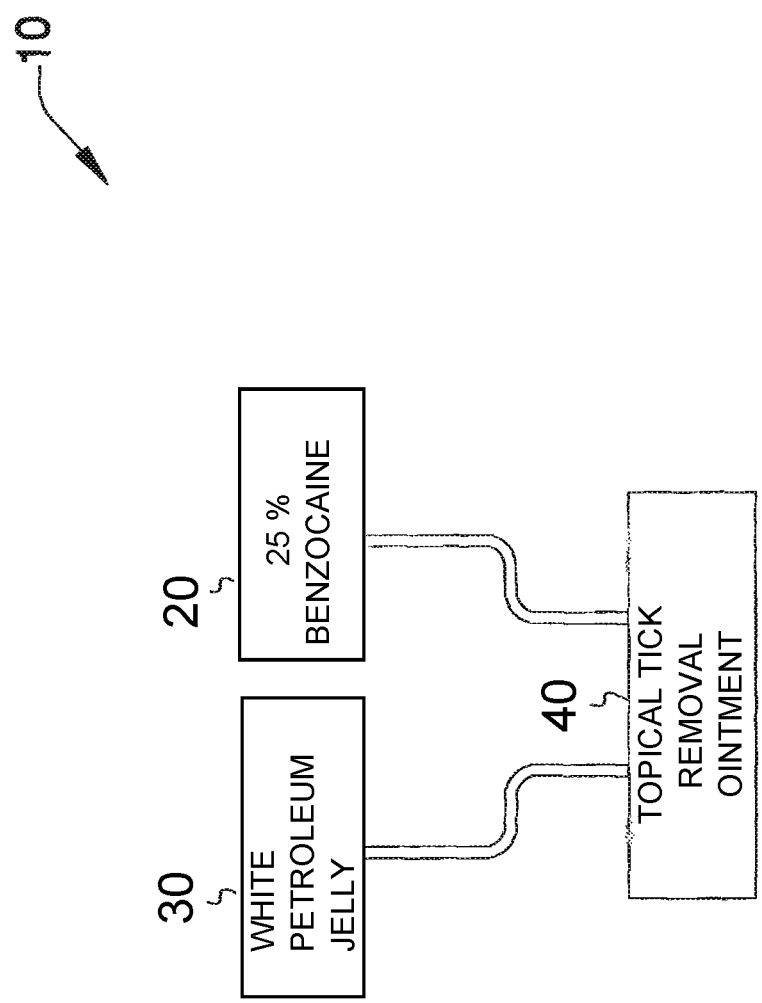

TICK REMOVAL OINTMENT

BACKGROUND OF THE INVENTION

Ticks, scientifically of the genus *Dermacentor* sp. from the Family Ixodidae, Order Acari, Class Arachnida, and phylum Arthropoda, host and transmit a number of various disease related bacteria and microbial pathogens for humans and animals. The microbial pathogens include rickettsial bacterium which causes Erhilchiosis, *borrelia hermsli* which causes relapsing fever, *francisella tularensis* which causes tularemia 35, known also as rabbit fever or deer fly fever, and ixodes scapularis and ixodes pacificus which serve as vectors for the Lyme disease pathogen, *Borrelia burgdoferi*, in the United States. Various types of compositions for the removal of ticks attached to a mammal are known in the prior art. Some of the prior tick removal techniques involve removal with various chemicals, which can present adverse reactions, or by the application of heat, which can potentially burn the host's skin. Other tick removal compositions employ an aerosol coolant spray, which while not presenting any direct danger to the host, involves the release of environmentally harmful volatile organic compounds into the Earth's atmosphere. An owner of a mammal, such as a pet dog or cat, is rightfully concerned about checking the pet for ticks embedded in the pet's skin due to the potential for pet's being infected with Lyme disease, cytauxzoonosis, babesiosis, tularemia, and other diseases which can lead to severe health issues and even death What is needed is a cost-effective topical composition for tick removal in the form on an ointment which will effectively and quickly remove a tick embedded in the mammal's skin without manual removal of the tick. The present tick removal ointment is a topical composition which includes 25% benzocaine incorporated in white petroleum jelly to maintain the topical composition in contact with a tick embedded in the mammal's skin and/or the mammal until the tick withdraws from the mammal and dies after the tick withdraws from the host. The present tick removal ointment, when topically applied to the tick embedded in the skin of the mammal, contains an effective amount of benzocaine to rapidly numb the tick and to extricate the tick upon the tick's self- release from the mammal's skin when the tick is numb and an effective amount of white petroleum jelly to kill the tick upon the tick's self-extrication.

FIELD OF THE INVENTION

The present invention relates to compositions for the expeditious and effective removal of ticks embedded in a host mammal's skin, and more particularly, to a topical tick removal ointment composition having 25% benzocaine incorporated in white petroleum jelly.

SUMMARY OF THE INVENTION

The general purpose of the present tick removal ointment, described subsequently in greater detail, is to provide a tick removal ointment which has many novel features that result in a tick removal ointment which is not anticipated, rendered obvious, suggested, or even implied by prior art, either alone or in combination thereof.

To accomplish this, the present tick removal ointment provides a new, cost effective composition for the removal of a tick from the skin of a host mammal, such as a pet dog or cat. When a tick embeds in the skin of the host mammal, the potential for harm to the host animal is present because the tick is prone to carry a wide range of infectious, potentially fatal diseases, such as Lyme disease, Rocky Mounted Spotted Fever, and tuleramia. The present tick removal ointment is a topical composition having 25% benzocaine incorporated in white petroleum jelly. The amount of benzocaine in the tick removal ointment is efficacious for numbing the tick and hence causes the tick to release or self-extricate from the host mammal, optimally prior to the transmission of disease organisms from the arthropod to the host mammal. Upon the self-extrication of the tick from the host mammal, the white petroleum jelly is efficacious for killing the tick. Application of the present tick removal ointment eliminates the need to make direct contact with the tick to remove the tick and further eliminates the task of observing the mammal for a period of time because the composition is devised to first release the tick from the host mammal and then to kill the tick once the tick is released from the host mammal.

Thus has been broadly outlined the more important features of the present tick removal ointment so that the detailed description thereof that follows may be better understood and in order that the present contribution to the art may be better appreciated.

BRIEF DESCRIPTION OF THE DRAWINGS

FIGURES

FIG. 1 is a block diagram of ingredients for a topical composition of a tick removal ointment.

DETAILED DESCRIPTION OF THE DRAWINGS

With reference now to the drawings, and in particular FIG. 1 thereof, an example of the instant tick removal ointment employing the principles and concepts of the present tick removal ointment and generally designated by the reference number 10 will be described.

Referring to FIG. 1 the ingredients for the composition of the present tick removal ointment 10 is illustrated. The tick removal ointment 10 is a topical composition which includes 25% benzocaine 20 incorporated in white petroleum jelly 30. Benzocaine is a local anesthetic composition to maintain the topical composition in contact with a tick embedded in the mammal's skin and/or the mammal until the tick withdraws from the mammal and dies after the tick withdraws from the host. The present tick removal ointment 10, when topically applied to the tick embedded in the skin of the mammal, contains an effective amount of benzocaine 20 to rapidly numb the tick and to self-extricate the tick from the mammal's skin when the tick is numb and an effective amount of white petroleum jelly 30 to kill the tick upon the tick's self-extrication. The tick removal ointment 10 can be provided in a tube or other container for access in order to apply the tick removal ointment onto the tick in-situ on the mammal.

What is claimed is:

1. A method of tick removal using an ointment, the method comprising:
   providing a topical composition comprising 25% benzocaine incorporated in white petroleum jelly; and
   applying the topical composition to a tick attached to a host mammal wherein the benzocaine numbs the tick such that the tick releases from the host mammal and is positioned within the topical composition such that the tick is killed by the white petroleum jelly.

* * * * *